United States Patent
Haque et al.

(12) 
(10) Patent No.: US 6,406,706 B1
(45) Date of Patent: *Jun. 18, 2002

(54) USE OF α- AND β-SANTALOLS MAJOR CONSTITUENTS OF SANDAL WOOD OIL, IN THE TREATMENT OF WARTS, SKIN BLEMISHES AND OTHER VIRAL-INDUCED TUMORS

(75) Inventors: Malika H. Haque; Azeez U. Haque, both of Columbus, OH (US)

(73) Assignee: Haque, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/637,290

(22) Filed: Aug. 11, 2000

Related U.S. Application Data

(63) Continuation-in-part of application No. 09/145,121, filed on Sep. 2, 1998, now Pat. No. 6,132,756, which is a continuation-in-part of application No. 08/960,303, filed on Oct. 29, 1997, now Pat. No. 5,945,116.
(60) Provisional application No. 60/030,307, filed on Nov. 5, 1996.

(51) Int. Cl.$^7$ ................................................. A61K 9/02
(52) U.S. Cl. ....................................... 424/400; 514/729
(58) Field of Search ............................... 424/400, 430; 514/729

(56) References Cited

U.S. PATENT DOCUMENTS

| | | |
|---|---|---|
| 4,908,355 A | 3/1990 | Gettings et al. |
| 5,532,215 A | 7/1996 | Lexdey et al. .................. 514/8 |
| 5,541,058 A | 7/1996 | Kreider et al. .................. 435/5 |
| 5,562,900 A | 10/1996 | Boyer et al. ................. 424/115 |
| 5,693,327 A | 12/1997 | Shah |
| 5,916,573 A | 6/1999 | Spiers et al. |

FOREIGN PATENT DOCUMENTS

| | | |
|---|---|---|
| CH | 688 787 A | 3/1998 |
| DE | 26 54 743 A | 6/1978 |

OTHER PUBLICATIONS

Printed advertisement for Occlusal–HP, www.genderm.co,, GenDerm Corporation, 1996.
Copy of label and instructions for DuoFilm, Schering–Plough HealthCare Products, 1995.
Brochure for DuoFilm, Schering–Plough HealthCare Products, Inc., 1996.
Principles and Practice of Pediatrics, Second Edition, J.B. Lippincott Company, 1994, Chapter 35, p. 903.
Atlas of Pediatric Dermatology, Lumps and Bumps, Wolfe, 1993, pp 5.5–5.7.
Color Textbook of Pediatric Dermatology, Second Edition, Viral Infections, Mosby, 1996, pp. 121–127.
Rudolph's Pediatrics, 20th Edition, Viral Infections, Simon & Shuster Company, 1996, p. 937–938.

Textbook of Pediatric Infectious Diseases, Edition 4, vol. 1, Viral and Fungal Skin Infections, W.B. Saunders Company, 1998, pp. 759–763.

WPI Abstracts, Section Ch, Week 1997 10, Derwent Publications Ltd., Class B05, An 1997–103645, XP 00 2131419 & JP 08 337520A, Tanaka, T. 1996.

Database CAPLUS on STN, AN 1996:226082, abstract of JP 08026980, 1996.

Database Medline on CAS, European Journal of Cancer Prevention, Dwivedi et al., "Chemopreventive effects of sandalwood oil on skin papillomas in mice", 6(4):399–401, Aug., 1996.

Dwivedl; Voss et al., Chemopreventive Effects of α–santalol on Skin Tumor Development in Mice, College of Pharmacy, South Dakota State University, Brookings, SD 57007, 1 paragraph abstract from the Proceedings of the American Association for Cancer Research, vol. 40, Mar. 1999.

*Primary Examiner*—Diana Dudash
*Assistant Examiner*—Alysia Berman
(74) *Attorney, Agent, or Firm*—Standley & Gilcrest LLP

(57) ABSTRACT

The present invention provides a method for the treatment of viral-induced tumors in mammals, more specifically, human warts. The method uses α- and β-santalols, or mixtures or derivatives thereof, to prepare medicaments for the treatment of viral-induced tumors i.e., warts caused by the human papillomavirus (HPV) in humans. The method of the invention comprises the topical administration of α- and β-santalols, or mixtures or derivatives thereof, in a composition derived therefrom, to the human epidermis, as needed. The present invention is also concerned with a unique antiviral composition useful for topical application. The antiviral composition according to this invention is also effective against other DNA viruses such as the DNA pox virus that causes *Molluscum contagiosum* and may be effective against other DNA viruses such as AIDS virus and RNA viruses. The α- and β-santalols composition, or mixtures or derivatives thereof, may also be effective in the treatment of genital warts and HPV of the genital tract and in the treatment of cancer of the skin and cervix. The α- and β-santalols, or mixtures or derivatives thereof, may also be effective in the prevention of dryness of the skin, rashes and flakiness associated with seborrheic dermatitis, psoriasis and allergic or eczematous rashes of the skin. The α- and β-santalols, or mixtures or derivatives thereof, may also be effective in the treatment of acne lesions of the face and the body and in the eradication of pustular acne lesions caused by staphylococcal acne and streptococcal bacterial infections.

6 Claims, No Drawings

USE OF α- AND β-SANTALOLS MAJOR CONSTITUENTS OF SANDAL WOOD OIL, IN THE TREATMENT OF WARTS, SKIN BLEMISHES AND OTHER VIRAL-INDUCED TUMORS

This application is a continuation-in-part of U.S. Ser. No. 09/145,121 filed Sep. 2, 1998, now U.S. Pat. No. 6,132,756, which itself is a continuation-in-part of U.S. Ser. No. 08/960, 303 filed Oct. 29, 1997, now U.S. Pat. No. 5,945,116, which claimed the benefit of U.S. Provisional Application No. 60/030,307 filed Nov. 5, 1996.

TECHNICAL FIELD

The present invention generally relates to therapeutic agents for the treatment of viral-induced tumors, such as warts. In one embodiment, the therapeutic agent is in the form of sandalwood oil or an isolate or isolates from the sandalwood oil described herein. Use of the oil or its components as a topical agent for the treatment of viral-induced tumors, such as human papillomavirus-induced tumors, is disclosed. The therapeutic agents in sandalwood oil were found to be α- and β-santalols. Use of α- and β-santalols in the treatment of viral-induced tumors, such as human papillomavirus-induced tumors, is disclosed.

BACKGROUND OF THE INVENTION

Viruses, which induce tumors in mammals, are widespread. Indeed, there are over sixty known types of human papillomaviruses (HPV) which are DNA viruses. These viruses may induce the production of tumors. Some of these HPV's have been associated with benign tumors, such as common warts, while others have been strongly implicated as etiologic agents in dysplasia and carcinomas in the oral and genital mucosa of the infected mammal.

Warts are a very common skin lesion in humans and are caused by various human papillomaviruses (DNA virus). Each virus is related to a specific clinical presentation of the wart. Warts are infectious and may be autoinoculated and spread to other individuals by direct contact.

Verrucae warts have a rough surface, are lumpy and typically flesh colored. Finger-like projections and sometimes dark specks are present, which are the result of thrombosed capillaries. Usually these warts are found on the face and scalp. Plantar warts are found on the planter surface of the feet and may be deep and painful. These warts occur singularly or in clusters and may be spread over a wide area. Flat warts are typically small, flat-topped, flesh colored papules that occur primarily on the face, hands and forearms. Usually the surface of the wart is smooth and they may appear in the hundreds. Genital warts are soft, flesh colored or slightly pigmented and occur in the genitalia of the mammal and may be sexually transmitted. Chronic infections that cause genital warts in women are a serious problem as intra epithelial neoplasia or squamous cell carcinoma may develop. See Oski et al., *Princ. Pract. Pediatrics*, 2nd ed., pp. 789–790.

There are various therapies for the treatment of warts, but none are considered truly effective as they typically fail to totally cure the lesions and do not prevent recurrence. A discussion of presently accepted therapies may be found in Stone, 1995, Cl. *Infec. Diseases*, Suppl. 20, pp. 991–997 and Sterling, 1995, *Practioner*, Jan. 239(1546), pp. 44–47. Numerous compositions are presently marketed for wart removal. One such product is Occlusal®—HP marketed by the GenDerm Corporation of Lincolnshire, Ill. This product is a 17% solution of salicylic acid in a polyacrylic vehicle. The Shering-Plough Company of Memphis, Tenn. produces and markets a product known as Duo Film® which is a patch containing salicylic acid. The product literature recommends that the wart be washed and dried prior to the application of a medicated patch which contains 40% salicylic acid. This patch is then covered with an additional bandage and the procedure is repeated every 48 hours until the wart is gone, which sometimes takes up to 12 weeks.

Recently, it has also been observed that individuals with depressed immune systems, such as sufferers of Acquired Immune Deficiency Syndrome (AIDS), may be prone to HPV infections which may result in tumor growth over their entire bodies, resulting in great mental and physical distress to the afflicted individual.

Current modalities for the treatment of viral-induced tumors involve the removal of the tumor by either: (1) surgical intervention (laser or operative); (2) the application of organic acids, such as glacial acetic acid and/or salicylic acid and lactic acid to "burn" the tumor away; (3) the injection into the tumor of an anti-tumor vaccine prepared from ground tumors; and to a lesser extent, (4) the use of a drug, such as podophyllin, interferons and fluorouracil or 5-FU; and (5) freezing.

While being useful for removing the viral-induced tumor, the current treatment modalities still suffer from one or more of the following drawbacks: (1) they may result in the destruction of healthy uninfected tissue; (2) they may result in scarring and disfigurement; (3) they may result in discomfort to the mammal being treated thereby; (4) they may result in necrosis of the tumor and the surrounding tissue may result in a secondary infection which may require treatment with an antibiotic; and (5) they do not always result in the destruction of latent viral DNA which may be maintained in surrounding tissues. Furthermore with these conventional treatments, subjects suffer from significant local, and at times, systemic side effects, incomplete resolution and frequent recurrences of the tumors, and of course, the expense incurred.

It is also known that phototherapy is used for removing laryngeal papillomatosis tumors. While such phototherapy reduces tumor growth by about 50%, it also results in a generalized skin photosensitivity for at least six weeks, as well as other minor reactions. Despite the apparent success of this technique, the presence of latent viral DNA is nonetheless still maintained in the surrounding tissues.

An article by B. M. Lawrence entitled "Progress in Essential Oils", *Perfumer & Flavorist*, Vol. 16, 49–58 (1991) reviews the work of several investigators on the chemical composition of sandalwood oil. This article reports on several of the oxidation products of the oil and compares the composition of Chinese sandalwood oil and Indian sandalwood oil. The santalol content (santalol, cis-α and cis-β, comprises about 50 and 20% respectively by weight of sandalwood oil) of various species of the genus Santalum, are also disclosed. This article makes no suggestion that sandalwood oil would be effective in treating the common wart in humans.

An article by Dwivedi et al. entitled, "Chemopreventive effects of sandalwood oil on skin papillomas in mice" in the *European Journal of Cancer Prevention* 1997; 6(4): 399–401, reports that the essential oil, emulsion or paste of sandalwood (*Santalum album L*) has been used in India as an ayruvedic medicinal agent. In his investigation, a 5% w/v solution of sandalwood oil in acetone was shown to be a chemopreventive agent against 7, 12-dimethylbenz(a)

anthracene initiated and 12-O-tetracecanoyl phorbol-13-acetate promoted skin papillomas in CD1 mice. The author suggests that sandalwood oil could be an effective chemopreventive agent against skin cancer.

None of these references suggest or disclose the use of α- and β-santalols, sandalwood oil, or a soap containing sandalwood oil as an agent for the treatment of human papillomavirus-induced tumors. There presently exists in the medical community a need for improved methods and compositions which provide therapeutic treatment of viral-induced tumors such as warts in humans. The present invention fills that need of the medical community.

SUMMARY OF THE INVENTION

One aspect of the present invention relates to the use of α- and β-santalols, or mixtures thereof, the active ingredients of sandalwood oil, for the treatment of viral-induced tumors. Another aspect of the invention relates to the use of α- and β-santalols, or mixtures thereof, to treat viral-induced tumors in mammals, especially humans. Yet anther aspect of the invention relates to the use of α- and β-santalols, the major constituents of sandalwood oil, in the treatment of warts, skin blemishes and other viral-induced tumors. One major benefit of the present invention is that that α- and β-santalols do not destroy healthy, uninfected tissues nor cause any systemic side effects or local side effects such as irritation, necrosis of tissue surrounding the wart, allergic rashes, scarring, disfigurement or discomfort to the human treated therewith. In fact, the use of α- and β-santalols, sandalwood oil or a soap containing the oil has been found to smooth the patient's skin and is beneficial to healthy tissue.

There is further disclosed a method for the prevention and treatment of genital warts, cancer of the cervix and eradication of human papillomavirus from the female genital tract in infected females, comprising the application of a cream or douche containing α- or β-santalols or mixtures or derivatives thereof, to the affected area of the human body. There is also disclosed a method for preventing cancer of the cervix, said method comprising the application of α- or β-santalols or mixtures or derivatives thereof, to the genital area of a female for a period of time and at a sufficient concentration to eradicate the human papillomavirus from the genital area of the female.

Another aspect of the present invention is directed to a simple method for providing therapeutic treatment of viral-induced tumors in humans. An additional aspect of the present invention relates to a method for the destruction of latent viral DNA which is contained in tissues so as to prevent recurrence of these tumors.

Thus, there is disclosed a method for the treatment of viral induced tumors in a mammal, said method comprising the topical application of α- and β-santalols and mixtures thereof.

The method of this invention is specifically directed to the use of a composition that is suitable for topical application. The initial discovery of the inventors was based upon the use of a soap manufactured by Karnataka Soaps & Detergents, Ltd., Bangalore, India, known and marketed as "Mysore Sandal Soap". The product packaging states that this soap contains natural Mysore sandalwood oil distilled by the government of Karnataka. It is known that this soap also contains vegetable ingredients. A second soap manufactured by Alfa Cosmetics, of Bombay, India, known as "Eastern Mysore's Pure Sandal Soap" has also been found effective in treating viral induced epidermal tumors, however, it is somewhat less effective. The "Eastern Mysore's Pure Sandal Soap" lists as its ingredients: palm stearin, rice bran fatty, coconut oil, caustic soda, perfume, sandalwood oil and preservatives. At the time the parent patent application was filed, the inventors had not isolated the active component from the sandalwood soap. Then after filing a continuation-in-part application, the inventors, through further investigative effort, had determined that the sandalwood oil component of the soap was responsible for its therapeutic effects. As of the filing date of the present application, the inventors have isolated the active ingredients from the sandalwood oil, α- and β-santalols. Analysis has led to the discovery that α- and β-santalols are the active components in sandalwood oil. As will be set forth below, the inventors have elucidated that the α- and β-santalols may be the agents with outstanding use in the treatment of human warts.

Approximately 70% of sandalwood oil is comprised of two bicyclic sequiterpene alcohols termed α- and β-santalols. Table I sets forth the constituents of sandalwood oil.

TABLE I

Composition of Sandalwood Oil

| Compound | Weight Percentage Composition |
| --- | --- |
| santene | 0.01 |
| α-pinene* | — |
| camphene* | — |
| acetic acid | — |
| teresantalal | — |
| α-santalene | 0.82 |
| trans-α-bergamotene | 0.12 |
| epi-β-santalene | 0.97 |
| β-santalene | 1.40 |
| γ-curcumene | 0.04 |
| β-bisabolene | 0.07 |
| β-curcumene | 0.13 |
| α-eka-santalal | 0.07 |
| ar-curcumene | 0.26 |
| β-eka-santalal | 0.01 |
| (E)-nerolidol | 0.06 |
| β-bisabolol | 0.64 |
| α-santalal | 2.90 |
| (Z)trans-α-bergamotal | 0.10 |
| α-bisabolol | 0.26 |
| cis-α-santalyl acetate | — |
| β-santalal | 0.56 |
| dihydro-α-santalol | 0.38 |
| cis-β-santalyl acetate | — |
| cis-α-santalol | 50.00 |
| (Z)-trans-α-begamotol | 3.90 |
| nuciferyl acetate+ | — |
| trans-α-santalol | 0.56 |
| epi-β-santalol | 4.10 |
| cis-β-santalol | 20.90 |
| trans-β-santalol | 1.50 |
| cis-lanceol | 1.70 |
| cis-nuciferol | 1.10 |
| spirosantalol | 1.20 |

*presumed impurities
+probably cis-nuciferyl acetate

The chemical make-up of a sandalwood oil varies slightly from source to source, however, α- and β-santalol make up over 65% of the oil.

The chemical formula for α- and β-santalol is $C_{15}H_{24}O$ and the chemical structures are shown below.

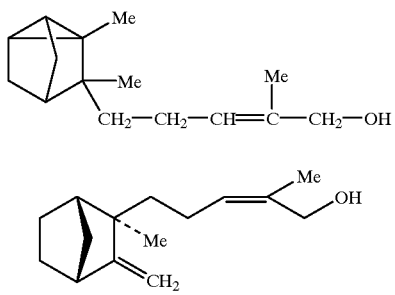

α-santalol

β-santalol

Santalols may be obtained by fractional distillation of sandalwood oil, with the α- and β-isomers appearing in different ratios and with the α-isomer being more abundant. The santalols are colorless to pale yellow in appearance. One source of availability is Aldrich Chemical Company in Milwaukee, Wis. They sell the santalols as a mixture of α- and β-isomers in the ratio of 2.5 to 1, respectively.

Santalols are commonly used in the flavor and fragrance industries and are considered woody, cedar-like, warm and herbaceous. They may be used in perfumes, baked goods, frozen dairy, soft candy, gelatin pudding, chewing gum and non-alcoholic beverages. As such, they are non-toxic and harmless when used either for external application on the skin or internal consumption for flavor.

The purpose of the present invention is to test the efficacy of α- and β-santalols in the treatment of warts, as a natural continuation of sandalwood oil, which in the earlier study was shown to be efficient in the treatment of warts.

In another embodiment of this invention, the active component or components of the sandalwood oil are disclosed for the treatment of viral-induced tumors.

In particular, the α- and β-santalols described herein may be used for the preparation of therapeutic compositions in the treatment of viral-induced tumors in humans. Preferably, the compositions useful in the method may be topically applied to the human in need of such therapy.

The method of the present invention neither destroys healthy, uninfected tissue nor results in any local or systemic side effects, scarring, disfigurement or discomfort to the human treated. Furthermore, the use of the present method results in the destruction of latent viral DNA found in the tumor and the surrounding tissues so that instances of incomplete resolution and tumor recurrence may be prevented. The method includes the use of α- and β-santalols for the administration to an area of the human which is anticipated to evidence viral-induced tumor growth, or an area which presently exhibits viral-induced tumor growth (i.e., warts and Molluscom contagiosum tumors) to eliminate the viral-induced tumor. In accordance with the method according to this invention, regular use of the α- and β-santalols is meant to mean application of the α- and β-santalols at least once a day to the body surface containing the viral-induced tumors (i.e., warts and *Molluscom contagiosum* tumors). A further embodiment of the method of this invention comprises washing the affected area of the body with the soap, rinsing the area, placing a small amount of the α- and β-santalols on the tumor to be treated and then gently rubbing to facilitate penetration. It has been determined through clinical evaluation that once the method of this invention is initiated, the warts begin to shrink, no matter what size, and will totally disappear after a period of 8 to 10 weeks of treatment.

DESCRIPTION OF PREFERRED EMBODIMENTS

The present invention is based, in part, on the discovery that a commercially available soap manufactured by the aforementioned companies may be useful in the treatment of viral-induced tumors in humans. Specifically, the invention is directed to the discovery that sandalwood oil is the active component of the soap and more specifically, that α- and β-santalols are the active ingredients in sandalwood oil.

As set forth below α- and β-santalols, and mixtures thereof, were found effective against human viral-induced tumors.

EXAMPLE 1

A 59-year-old female developed six warts on her left hand that were persistent over a year despite use of over-the-counter conventional treatments. Four of the warts were on the wrist with sizes approximately 3 mm×3 mm×2 mm. The wart on the thumb was approximately 4 mm×3 mm×2 mm in size and the one on the palm below the thumb was about 3 mm×2 mm×2 mm in size.

The subject was advised to rub 1 drop of the santalol mixture after washing her hand with regular soap and water. The subject was to use a loofah sponge to soften the surface of the warts prior to the application of the santalol mixture. After a week of such treatment, the warts began to lessen in size and were completely eradicated in ten weeks. There was no evidence of any local skin irritation, such as redness, pain, etc., nor any systemic side effects. The treatment was well tolerated.

EXAMPLE 2

A 26-year-old male subject had three warts on his right and left index fingers for over five years. One of the left index finger warts measured 8 mm×5 mm×4 mm and another measured 6 mm×4 mm×3 mm in size. The right index finger wart measured 5 mm×4 mm×3 mm. The subject was advised to wash the warts with soap and water using a loofah sponge to soften the surface of the warts, prior to applying one drop of the santalol mixture on the warts and rubbing gently. The treatment was to occur once a day.

Two weeks after such application, the warts started getting smaller and they developed a dark color. In eight weeks, the warts were eradicated. The treatment was well tolerated with no evidence of any local side effects such as redness, irritation or pain and with no systemic side effects.

EXAMPLE 3

A 5-year-old female subject developed a large wart around her right nostril in May 1998. Her pediatrician referred her to a plastic surgeon who surgically removed it under sedation in August 1998. The wart started growing back again in December 1998. She also developed additional warts on her hands. In May 1999, the plastic surgeon removed the warts on her hands and nose using laser surgery under general anesthesia. After about four months, the warts began growing back again. The warts increased in number and size around her nose, lips, right knee and right foot. The subject was seen by the plastic surgeon again in October 1999 and the family of the subject was told that he was not able to surgically treat her warts anymore and the surgeon advised them to seek another type of treatment elsewhere.

When the subject was seen by the inventor for the santalol treatment, she had 21 warts on her face. They were on her nose, around her nose and on her lips and the warts varied in size from about 4 mm×3 mm×2 mm to about 8 mm×5 mm×5 mm. There was a large wart close to her upper eyelid that measured 4 mm×3 mm×3 mm in size. This 5-year-old also had warts on her right knee, foot, arm and both hands. The subject was asked to wash the warts on her face with soap and water and then apply the santalols with a cotton swab. As the treatment progressed, the warts on her face began shrinking in size and in about 6 weeks of such treatment the warts were resolved completely leaving the subject with clear skin. There was no evidence, at the sites of application of the santalols, of any skin irritation, of any burning or redness or of any systemic side effects.

After the resolution of the facial warts, the subject's non-facial warts were treated with the santalols. Within three weeks the non-facial warts were completely resolved.

In light of these results, the inventors have concluded that α- and β-santalols, the major constituents of sandalwood oil, are the active components that may be used to eradicate viral tumors, such as DNA-human papillomaviruses (HPV)-causing warts in different parts of the human body. Additionally, α- and β-santalols may be useful for other viral-induced tumors in different parts of the human body, including, genital warts, human papillomaviruses (HPV) of the female genital tract and the DNA pox virus causing *Molluscum contagiosum*. The santalols have an anti-viral and anti-tumor effect.

Other Indications

It is proposed that the continued use of α- and β-santalols would be effective for the treatment of other viral tumors caused by DNA and RNA viruses and the eradication of bacterial infections such as those caused by streptococci or staphylococci.

During the clinical evaluation of the present invention, it has come to the attention of the inventors that the sandal soap, sandalwood oil, and α- and β-santalols may also be effective in preventing dryness of the skin. Thus, the sandal soap, sandalwood oil and α- and β-santalols described herein have also been found effective in preventing the flakiness and dryness associated with skin that is constantly subject to harsh detergents. In addition, the sandal soaps have been shown to be active against seborrheic dermatitis, psoriasis, eczema and skin allergies.

It is quite evident from the clinical experience to date, that the α- and β-santalols of the present invention have been outstandingly effective in the treatment and elimination of warts. The complete eradication of the warts with no recurrence is truly a surprising result as the medical community still searches for a cost effective and efficacious method to control this human malady.

Industrial Applicability

Viral-induced tumors, especially of the skin, are very common. These tumors are typically very difficult to treat, control and prevent. The medical community has searched for decades for new therapies to treat this common human malady. The present invention provides a simple and cost-effective method to treat these viral-induced tumors.

Many modifications may be made to the invention herein without departing from the basic spirit or scope of the invention. Accordingly, it will be appreciated by those skilled in the art, that within the scope of the appended claims, the invention may be practiced by means other than has been specifically described herein.

We claim:

1. A method for the treatment of human papillomaviruses (HPV)-induced tumors in a mammal said method comprising the topical application of a composition to the affected area selected from the group consisting of α- and β-santalols, and mixtures thereof, to said mammal.

2. The method according to claim 1 wherein said human papillomaviruses (HPV)-induced tumor is selected from the group consisting of verrucae warts, plantar warts, flat warts, genital warts and *Molluscum contagiosum*.

3. The method according to claim 1, wherein said α- and β-santalols are obtained from at least one Santalum species selected from the group consisting of *S. album, S. yasi, S. papuanum* and *S. spicatum*.

4. A method for the treatment of genital warts, and treatment of human papillomavirus (HPV) in the female genital tract in infected females comprising the application of a composition to the affected area, in the form of a cream or a douche, selected from the group consisting of α- and β-santalols, and mixtures thereof.

5. The method according to claim 1, wherein said mammal is a human.

6. The method according to claim 1, wherein said composition is in an admixture with a pharmaceutically acceptable carrier or excepient.

* * * * *